United States Patent [19]
Griffith

[11] Patent Number: 5,249,580
[45] Date of Patent: Oct. 5, 1993

[54] METHOD FOR ULTRASOUND IMAGING

[76] Inventor: James M. Griffith, P.O. Box 15337, Newport Beach, Calif. 92659

[21] Appl. No.: 11,335

[22] Filed: Jan. 29, 1993

Related U.S. Application Data

[62] Division of Ser. No. 773,037, Oct. 8, 1991, Pat. No. 5,201,315.

[51] Int. Cl.$^5$ ............................................. A61B 8/12
[52] U.S. Cl. .................... 128/662.06; 128/772; 128/898
[58] Field of Search ............... 128/662.03, 662.06, 128/772, 898, 4; 604/280

[56] References Cited

U.S. PATENT DOCUMENTS

| | | | |
|---|---|---|---|
| 4,762,129 | 8/1988 | Bonzel | 128/344 |
| 4,794,931 | 1/1989 | Yock | 128/660.03 |
| 4,815,470 | 3/1989 | Curtis et al. | 128/662.03 |
| 4,889,128 | 12/1989 | Miller | 128/662.06 |
| 4,899,757 | 2/1990 | Pope, Jr. et al. | 128/662.06 |
| 4,917,097 | 4/1990 | Proudian et al. | 128/662.06 |
| 4,951,677 | 8/1990 | Crowley et al. | 128/662.06 |
| 5,000,185 | 3/1991 | Yock | 128/662.03 |
| 5,024,234 | 6/1991 | Leary et al. | 128/663.01 |
| 5,046,503 | 9/1991 | Schneiderman | 128/692 |
| 5,090,958 | 2/1992 | Sahota | 604/98 |
| 5,178,150 | 1/1993 | Silverstein et al. | 128/662.06 |
| 5,179,961 | 1/1993 | Littleford et al. | 128/772 |

OTHER PUBLICATIONS

Brochure "Get The Inside View", InterTherapy.
Bruchure "Proformer Guiding Catheters—New Products for AHA 1992", Mansfield Boston Scientific Corporation.

Primary Examiner—William E. Kamm
Assistant Examiner—George Manuel
Attorney, Agent, or Firm—Woodcock Washburn Kurtz Mackiewicz & Norris

[57] ABSTRACT

An ultrasound imaging method for invasive imaging, in particular for imaging blood vessels including the coronary vessels. A sheath is comprised of three lumens; one serves as an ultrasound probe passage, one serves as a guide wire passage, and one serves as either a probe or a guide wire passage and is connected to the other two. Methods of using the sheath disclosed to obtain ultrasound images of a region within a subject are disclosed.

4 Claims, 1 Drawing Sheet

METHOD FOR ULTRASOUND IMAGING

This is a division, of application Ser. No. 773,037, filed Oct. 8, 1991, now U.S. Pat. No. 5,201,315.

The present invention relates to obtaining ultrasound images of body cavities, lumens, or vessels and, particularly, to obtaining images of coronary arteries. The present invention discloses a sheath containing a guide wire lumen, an ultrasound probe lumen, and a lumen which alternately serves as a passage for either the guide wire or the probe.

BACKGROUND OF THE INVENTION

Invasive ultrasound imaging catheters are designed for use in conjunction with a guide wire. In the past, four different methods have been used to adapt the imaging catheter to a guide wire.

In the first method a guide wire tip is attached to the distal end of an imaging sheath and is known as a "fixed wire" design. This method has been used with mechanically rotated probes. The design, however, has two disadvantages, first, the wire cannot be left across a lesion while the imaging catheter is withdrawn and replaced with a different device, and secondly, fixed wire devices are more difficult to "steer" than the common "steerable" and "removable" guide wires. An example of a fixed wire tip is disclosed in U.S. Pat. No. 4,794,931—Yock.

A second type of catheter, known as transducer-array catheters, have been designed so that a guide wire can be threaded through a lumen which passes coaxially through the array. This design allows a user to place the imaging catheter over a guide wire by the same methods practiced with standard dilatation catheters. Transducer array catheters work with electronically scanned transducer arrays however this type of catheter design cannot be adapted for use with mechanically-rotated probes. An example of a transducer-array catheter is disclosed in U.S. Pat. No. 4,917,097—Proudian et al.

The third catheter design uses a dual lumen sheath. A lumen for the guide wire and a parallel lumen for a rotating ultrasound probe are provided. Unfortunately, the side-by-side positioning of the wire and probe lumens causes the catheter to be of a larger cross-section than is necessary for ultrasound imaging. Large catheters are disadvantageous because they reduce or stop blood flow in small or narrowed arteries. A product of this type is sold by Cardiovascular Imaging Systems, Inc. of Mountain View, Calif. (USA).

Finally, a fourth design for this type of catheter provides a single-lumen sheath positioned over a guide wire and across the section of the vessel to be imaged. The wire is then removed and "replaced" with an ultrasound probe. This design has the advantage of yielding a catheter diameter which is not much larger than the probe diameter. However, using the single-lumen sheath in conjunction with "over-the-wire" catheters is time consuming. For example, to remove the ultrasound catheter and position a dilatation catheter a user would first remove the probe, then position the guide wire and remove the sheath. Finally, the user would place the dilatation catheter over the wire. In contrast, a user can exchange one dilatation catheter for another by removing the first catheter and placing the second catheter over the wire. The time difference can be very important when working within the coronary arteries. An example of this type of device is sold by InterTherapy, Inc. of Santa Ana, Calif. (USA).

Thus, it can be seen that there is a long-felt yet unfilled need to provide a design which permits a catheter containing a mechanically rotated probe to be steered into place using a guide wire while maintaining a minimum cross-section.

SUMMARY OF THE INVENTION

An object of the invention is to provide a method for using improved sheaths.

Thus, in a preferred embodiment the present invention provides a flexible sheath for positioning an ultrasound imaging probe within a region of a vessel comprising a distal tip portion with a lumen adapted to accept a guide wire, a flexible single lumen intermediate section connected proximally to the distal tip portion, and a dual lumen region extending proximally from the flexible intermediate section. The dual lumen region comprises a wire lumen adapted to accept a guide wire and a probe lumen adapted to accept an ultrasound probe wherein the probe lumen and wire lumen connect with the single lumen intermediate section.

Most preferably, the sheath of the present invention includes a tapered flexible tip at the distal portion which has a lumen for accepting the guide wire and a radio opaque marker for X-ray viewing. Similarly, in certain preferred embodiments, a radio opaque marker for X-ray viewing will be disposed within the flexible intermediate section. Most preferably, the intermediate section lumen and the probe lumen are coaxial and the wire lumen is connected to the intermediate-section lumen at a tapered transition. Additionally, in certain embodiments of the present invention a three lumen section may also be provided in place of the proximal dual lumen section of the exemplary embodiment described herein.

The present invention also discloses methods of ultrasonically imaging a region of a subject by using an ultrasound probe, a guide wire and an ultrasound sheath substantially made in accordance with the present invention. The guide wire is advanced through the subject until the distal tip of the wire is distal to the region to be imaged and the intermediate portion of the sheath is then advanced over the wire until it has passed through the region to be imaged. The wire is then withdrawn from the single lumen portion of the sheath while holding the sheath stationary within the subject and leaving the distal tip of the wire within the dual lumen portion of the sheath. The ultrasound probe tip is next advanced into the intermediate portion of the sheath while holding the sheath stationary within the subject and the probe is activated to obtain ultrasound images.

In certain embodiments of the methods of the present invention a further step permitting additional over-the-wire invasive procedures to be performed are disclosed that include the steps of holding the sheath stationary and retracting the probe from the single lumen portion of the sheath and then advancing the wire through the sheath tip, whereby the distal tip of the wire is again disposed at a point beyond the region to be imaged. The wire is then held stationary and the sheath and the probe are retracted whereby the probe and sheath are removed from the subject thereby leaving the wire in place for additional procedures Also, certain methods of the present invention also permit recovery from ischemic episodes during use that include the steps of holding the sheath stationary within the subject, retracting the probe until it is disposed proximal to the single lumen, and advancing the wire through the single lumen. The wire is held stationary within the artery and the probe and sheath are withdrawn until the tip of the sheath is outside the narrow portion of the artery whereby increased blood flow occurs to combat the ischemia. After the ischemia episode passes, the above-described methods are undertaken at the step of advancing the sheath through the region to be imaged.

BRIEF DESCRIPTION OF THE DRAWINGS

The above and other objects and features of the present invention will appear after careful consideration of the preceding and following description including the drawings in which.

DETAILED DESCRIPTION OF THE PREFERRED EMBODIMENTS

Figure 1:
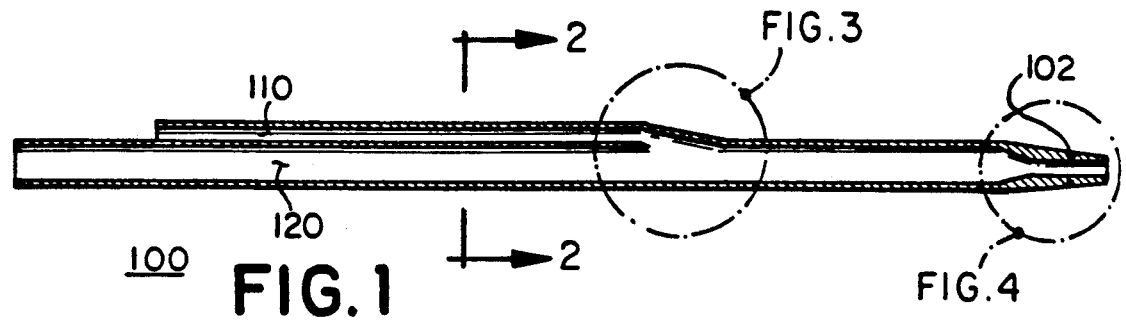
FIG. 1 is a longitudinal cross-section of the distal end of a sheath made in accordance with the present invention.

Referring now to FIG. 1, the distal portion of a sheath 100 made in accordance with the present invention is illustrated. Those of ordinary skill will understand that the sheath 100 is typically substantially tubular and that FIG. 1 illustrates a longitudinal cross-section of the sheath 100. Those of ordinary skill will further be familiar with the types of materials and methods used to manufacture sheaths such as those disclosed herein. Preferably, the sheath 100 of the present invention is lubricated on its exterior surface and may also be lubricated on its interior surface. Assuming a coronary artery imaging application, the complete sheath 100 is preferably about 1.5 meters long. The distal tip portion of the sheath is preferably about 1.0 cm long and is flexible so that it may be advanced over a guide wire that has been threaded through a coronary artery. The distal tip portion of the sheath 100 is soft and tapered as explained below with reference to FIG. 4 so that it is atraumatic to the artery. The inside diameter of the distal tip portion of the sheath is preferably tapered as shown. This taper permits a guide wire tip to move freely through the distal tip, which is preferably radio opaque or contains an opaque marker 102 to indicate the sheath-tip location in X-ray views. The inside diameter is most preferably sized to accept a guide wire and is about 15 or 20 mils across.

The intermediate section of the sheath adjoining the distal portion is a flexible elongated substantially tubular section that is also substantially transparent to the acoustic energy used for imaging. The interior diameter of the intermediate section of the sheath 100 is large enough to pass either a guide wire or an imaging probe. The outside diameter is preferably only a few thousandths of an inch larger than the interior diameter, thus the sheath wall in this region is relatively thin. A wide range of choices exist for selecting the length of this portion of the sheath 100; a short length, for example 1 cm, could be used. However, a longer length, for example 10 cm, allows image collection at various positions in the artery without repositioning the sheath 100.

The region of the sheath 100 near cross-sectional arrows 2—2 shown in FIG. 1 is comprised of flexible dual lumen tubing. A guide wire lumen 110 and a probe lumen 120 are disposed side-by-side so that a wire and a probe may simultaneously be inserted into this portion of the sheath 100. The diameters of the guide wire lumen 110 and probe lumen 120 are thus sized to accept the wire and probe. In a preferred embodiment, this section of the sheath 100 is generally at least 10-20 cm long so that the wire can be retracted from the distal portions of the sheath 100 without accidentally retracting it from the dual lumen region. It is also feasible to extend the dual lumen region of the sheath 100 to a length that includes the proximal end of the sheath 100, i.e., toward the left side of the sheath 100 illustrated in FIG. 1.

The transition area between the dual lumen region and the intermediate section is smoothly tapered to make the sheath 100 atraumatic to the artery being imaged. As explained below, this section of the sheath can also be marked so that it can be seen in X-ray views. However, those of ordinary skill will realize that the physical marker can be placed in the sections of the sheath closer to the proximal or distal ends but should be kept near the transition section so that the user can easily infer this section's location in the artery. FIG. 1 shows the probe lumen 120 connecting straight into the lumen of the intermediate section while the wire lumen 110 is offset. This is just one example of how the taper in the section near the dual lumen can be accomplished; either or both lumens 110,120 of the dual lumen region can be offset from the lumen in the intermediate section.

The proximal section of the sheath 100 is a single lumen tubing which passes the ultrasound probe. It extends from the dual lumen region to essentially the proximal end of the sheath 100.

Figure 2:
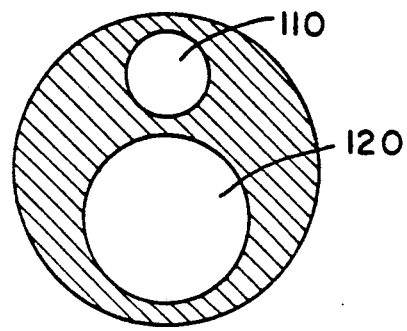
FIG. 2 is a cross-sectional view of the distal end of a sheath made according to the invention taken along line 2—2 of FIG. 1.

FIG. 2 shows the dual lumen region of the sheath in cross-section as indicated by arrows 2—2 in FIG. 1. The cross-section shows substantially circular inside and outside surfaces; however, it should be understood that other shapes could readily be used. From FIG. 2 one of ordinary skill can appreciate that the intermediate section is substantially smaller in cross-sectional area than the dual lumen region. Thus, with a given ultrasound probe diameter, the sheath of the present invention allows imaging in a smaller artery than is possible with a sheath design wherein the dual lumen region resides in the imaged portion of the artery. A numerical example is useful to illustrate this point. Assuming currently available probes and wires are used, a wire lumen 110 of about 0.016" (0.4 mm) and a probe lumen 120 of about 0.045" (1.1 mm) could be chosen. For reliability and construction ease, the minimum wall thicknesses in the sheath are at least several mils, for example 0.005" (0.1 mm). From these numbers it is possible to calculate the ratio, R, of the cross-sectional area of the dual lumen region of the sheath 100 with respect to the cross-sectional area of the sheath in the flexible intermediate section, thus:

$$R = \frac{(5 + 45 + 5 + 16 + 5)^2}{(5 + 45 + 5)^2} = 1.9$$

(Values in parentheses in mils).

The sheath design of the present invention therefore offers an advantage over previous designs that include the distal end of the guide wire lumen terminating in the distal tip. The advantage is that with the sheath 100 of the present invention a smaller cross-section is placed in the section of artery to be imaged, thereby reducing blood flow blockage. As ultrasound probes are made smaller the ratio R will become larger and the advantage increased.

Figure 3:
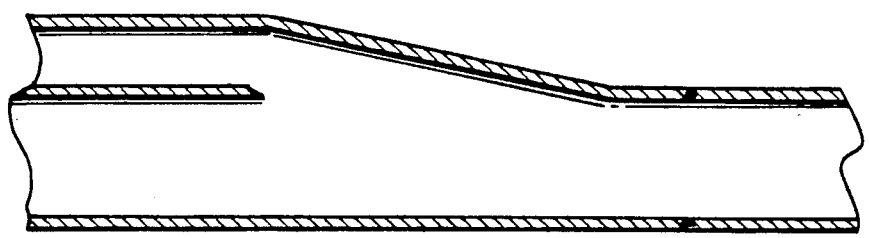
FIG. 3 is a partial view of the indicated portion of the sheath shown in FIG. 1 illustrating the transition region of the sheath.

FIG. 3 shows an enlarged view of the transition section where the wire lumen 110 and probe lumen 120 join. A location for a proximal radio opaque marker 104, as discussed above is also shown. The radio opaque marker 104 is preferably formed using a metallized band comprised of platinum or gold alloy.

Figure 4:
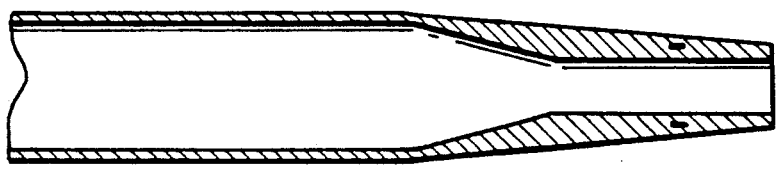
FIG. 4 is a partial view of the indicated portion of the sheath shown in FIG. 1 illustrating an atraumatic tip.

FIG. 4 shows an enlarged view of the distal tip portion of the sheath, which preferably includes a distal radio opaque marker 102 discussed above. The marker 102 can also be formed using a metal band.

The present invention also provides improved methods of obtaining images. Consider using the sheath of the present invention during a percutaneous transluminal coronary angioplasty (PTCA) procedure. An ultrasound probe is inserted into the probe lumen 120 with the probe tip proximal to the transition section. Doses of contrast media are supplied where needed to allow X-ray visualization and anatomic orientation. A guide wire is introduced through a guiding catheter and into the proper coronary artery. After the wire tip is positioned on the distal side of the restriction or lesion, the wire is used to guide the sheath 100 into the artery and through the stenosis. The flexible intermediate section is then placed within the stenosis using X-ray visualization, and the guide wire is retracted so that the distal tip of the wire resides in the wire lumen 110 and is clear of the intermediate section. The ultrasound imaging probe is then advanced into the intermediate section to obtain desired images. If the patient becomes ischemic before needed images are obtained, the probe tip can be extracted a short distance into the dual lumen section and the wire advanced through the distal tip of the sheath 100 into the artery. The sheath 100 and probe may then be retracted from the lesion and thereby allow increased blood flow through the lesion. When the ischemia passes, the sheath 100 and probe are repositioned and the needed images can then be obtained.

After obtaining images, the probe tip is drawn into the dual lumen region and the wire advanced a short distance through the sheath tip. The sheath 100 and probe are then withdrawn until outside the body and free from the wire. This last step leaves the wire and guiding catheter ready for use with a dilatation catheter. After the dilatation, additional images can be obtained by repeating the previously described steps.

The use of the present invention has been described in conjunction with a therapeutic PTCA procedure. It is understood, however, that the sheath 100 disclosed herein can also be used in conjunction with other invasive procedures or as part of a diagnostic procedure. Additionally, those of ordinary skill will realize that a third lumen could be incorporated proximal of the intermediate section into the sheath 100 illustrated and described. The sheath 100 could then be used to deliver other devices, probes or sensors and the like, permitting other signals or substances to be introduced into the patient, other parameters monitored or other therapies initiated. Thus, although the present invention has been described in what is presently considered the most practical and preferred embodiment it is to be understood that the invention is not to be limited to the disclosed embodiment. The invention is intended to cover various modifications and equivalent arrangements included within the spirit and scope of the appended claims.

What is claimed is:

1. A method for ultrasonically imaging a region of a subject comprising the steps of:

(a) providing an ultrasound probe, a guide wire, and an ultrasound imaging sheath, wherein the sheath comprises an elongate flexible member having a lumen in its distal length, the outside of the distal length being sized for passage into the region of the subject while the diameter of the lumen is sized to accept either the wire or the probe, wherein the lumen splits into a dual lumen at a point proximally disposed from said distal length of the imaging sheath, the dual lumen comprising a wire lumen sized to slidingly accept a guide wire, and a probe lumen is sized to slidingly accept a probe;

(b) positioning the distal end of the ultrasound probe within the dual lumen portion of the sheath while keeping the probe end at a point proximal of the single lumen portion of the sheath;

(c) advancing the guide wire through the subject until the distal tip of the wire is distal of the region of the subject to be imaged;

(d) advancing the sheath until the single lumen portion has passed through the region to be imaged;

(e) withdrawing the wire from the single lumen portion of the sheath while holding the sheath stationary within the subject, and leaving the distal tip of the wire within the dual lumen portion of sheath;

(f) advancing the ultrasound probe tip into the single lumen portion of the sheath while holding the sheath stationary within the subject; and (g) activating the probe to obtain ultrasound images by passing sound waves through the sheath's single lumen wall.

2. A method as in claim 1 further comprising the steps of:

performing an additional over-the-wire invasive procedure by holding the sheath stationary within the artery and retracting the probe from the single lumen portion of the sheath;

advancing the wire through the single lumen, whereby the distal tip of the wire is again disposed distal to the region to be imaged;

holding the wire stationary within the vessel;

retracting the sheath and probe, whereby the probe and sheath are removed from the subject; and leaving the wire in place for the performance of additional procedures.

3. A method as in claim 1 including steps for relieving an ischemic episode, further comprising the steps of:

holding the sheath stationary within the subject;

retracting the probe until it is disposed proximal of the single lumen;

advancing the wire through the single lumen;

holding the wire stationary within the artery;

withdrawing the probe and sheath until they are outside a portion of the artery having a reduced diameter, whereby increased blood flow occurs to combat the ischemia; and resuming imaging by the method of claim 1 after the ischemia passes.

4. A method of obtaining ultrasound images of an artery comprising the steps of:

(a) advancing a guide wire so that the distal tip of the guide wire is within the artery and distal of the portion of artery to be imaged;

(b) advancing an elongate sheath using the wire as a guidance device until the distal end of the sheath is within the artery and distal of the portion of artery to be imaged;

(c) retracting the wire until it becomes proximal of the region of the artery to be imaged;

(d) advancing an ultrasound probe until the tip is within the region of artery to be imaged;

(e) activating the probe to obtain ultrasound images.

* * * * *

Disclaimer 5,249,580 - James M. Griffith, Newport Beach, Calif. METHOD FOR ULTRASOUND IMAGING. Patent dated October 5, 1993. Disclaimer filed May 3, 1999, by the assignee, Boston Scientific Corporation.

Hereby enters this disclaimer to all claims of said patent.
*(Official Gazette,* June 22, 1999)